(12) United States Patent
Prieto et al.

(10) Patent No.: US 8,961,767 B2
(45) Date of Patent: Feb. 24, 2015

(54) SELF-ASSEMBLY OF COATINGS UTILIZING SURFACE CHARGE

(75) Inventors: Amy L. Prieto, Fort Collins, CO (US); Derek C. Johnson, Johnstown, CO (US); James M. Mosby, Fort Collins, CO (US)

(73) Assignee: Colorado State University Research Foundation, Fort Collins, CO (US)

(*) Notice: Subject to any disclaimer, the term of this patent is extended or adjusted under 35 U.S.C. 154(b) by 286 days.

(21) Appl. No.: 13/073,879

(22) Filed: Mar. 28, 2011

(65) Prior Publication Data

US 2012/0073971 A1 Mar. 29, 2012

Related U.S. Application Data

(60) Provisional application No. 61/318,068, filed on Mar. 26, 2010.

(51) Int. Cl.
  *B01D 59/42* (2006.01)
  *C25D 13/02* (2006.01)
  *H01M 4/04* (2006.01)
  (Continued)

(52) U.S. Cl.
  CPC ............... *C25D 13/02* (2013.01); *H01M 4/045* (2013.01); *H01M 4/1395* (2013.01); *H01M 10/052* (2013.01); *H01M 10/0562* (2013.01);
  (Continued)

(58) Field of Classification Search
  CPC ......... C25D 13/02; C25D 3/58; H01M 4/045; H01M 4/1395; H01M 10/052; H01M 10/0562; G01N 31/164; Y02E 60/122
  USPC .............. 204/490, 644, 548, 471; 429/218.1
  See application file for complete search history.

(56) References Cited

U.S. PATENT DOCUMENTS

| 3,664,939 A | 5/1972 | Luner et al. |
| 4,165,242 A | 8/1979 | Kelly et al. |

(Continued)

OTHER PUBLICATIONS

Sides et al., "Measurement of the Zeta Potential of Planar Solid Surfaces by Means of a Rotating Disk," Langmuir 2004, 20, 11493-11498.

(Continued)

*Primary Examiner* — Xiuyu Tai
(74) *Attorney, Agent, or Firm* — Samuel M. Freund; Cochran Freund & Young LLC

(57) ABSTRACT

An apparatus and method for measuring the isoelectric pH for materials deposited on or otherwise affixed onto and in contact with an electrode surface, and a method for utilizing the isoelectric pH to form nanometer thickness, self-assembled layers on the material, are described. Forming such layers utilizing information obtained about the isoelectric pH values of the substrate and the coating is advantageous since the growth of the coating is self-limiting because once the surface charge has been neutralized there is no longer a driving force for the solid electrolyte coating thickness to increase, and uniform coatings without pinhole defects will be produced because a local driving force for assembly will exist if any bare electrode material is exposed to the solution. The present self-assembly procedure, when combined with electrodeposition, may be used to increase the coating thickness. Self-assembly, with or without additional electrodeposition, allows intimate contact between the anode, electrolyte and cathode which is required for successful application to solid-state batteries, as an example.

3 Claims, 7 Drawing Sheets

(51) Int. Cl.
   *H01M 4/1395*       (2010.01)
   *H01M 10/052*       (2010.01)
   *H01M 10/0562*      (2010.01)
   *G01N 31/16*        (2006.01)
   *C25D 3/58*         (2006.01)

(52) U.S. Cl.
   CPC .......... *Y02E60/122* (2013.01); *G01N 31/164* (2013.01); *C25D 3/58* (2013.01)
   USPC .......... 204/490; 204/644; 204/548; 204/471; 429/218.1

(56) References Cited

U.S. PATENT DOCUMENTS

| | | |
   |---|---|---|
   | 4,234,404 A | 11/1980 | Satoh |
   | 4,588,492 A | 5/1986 | Bier |
   | 4,673,483 A | 6/1987 | Mandle |
   | 5,290,408 A | 3/1994 | Lewandowski et al. |
   | 5,298,143 A | 3/1994 | Ivory et al. |
   | 2005/0014151 A1 | 1/2005 | Textor et al. |
   | 2006/0110609 A1* | 5/2006 | Eaton et al. ............ 428/446 |
   | 2007/0020400 A1 | 1/2007 | Chang |
   | 2007/0163884 A1 | 7/2007 | Strand et al. |
   | 2011/0063369 A1* | 3/2011 | Okamura ............ 347/44 |

OTHER PUBLICATIONS

Mosby et al., "Direct Electrodeposition of Cu2Sb for Lithium-Ion Battery Anodes," J. Am. Chem. Soc. 2008, 130, 10656-10661.

Liu et al., "Understanding the Improvement in the Electrochemical Properties of Surface Modified 5 V LiMn1.42 Ni0.42Co0.16O4 Spinel Cathodes in Lithium-Ion Cells," Chem. Mater. 2009 21, 1695-1707.

* cited by examiner

SELF-ASSEMBLY OF COATINGS UTILIZING SURFACE CHARGE

CROSS-REFERENCE TO RELATED APPLICATIONS

The present application claims the benefit of U.S. Provisional Patent Application No. 61/318,068 for "Isoelectric Determination Apparatus and Use In The Fabrication Of Batteries" by Amy L. Prieto et al., which was filed on Mar. 26, 2010, the entire contents of which is hereby specifically incorporated by reference herein for all that it discloses and teaches.

BACKGROUND OF THE INVENTION

Secondary lithium-ion batteries have found multiple applications in portable electronics where high charge and discharge rates are not required to improve performance. However, high rates become important when considering the use of rechargeable lithium-ion batteries in the transportation industry. Electrode materials having irregular surfaces resulting in high interfacial surface areas and short characteristic diffusion lengths are expected to provide batteries with high power densities. Producing uniform, defect-free surface coatings for such electrodes for lithium-ion batteries having electrically insulating, but ionically conducting electrolytic separator materials on the nanoscale (for either the negative and/or positive electrodes), has proved to be difficult.

SUMMARY OF THE INVENTION

Self-assembly of surface coatings using electrostatic forces has not been widely pursued for high surface area structures in the past because of the difficulty in determining the isoelectric pH; that is, the pH at which there is no net surface charge.

Embodiments of the present invention overcome the disadvantages and limitations of the prior art by providing an apparatus and method for measuring the isoelectric pH of materials that can be deposited or otherwise affixed on and in electrical contact with an electrode surface.

It is further an object of embodiments of the present invention to provide a method utilizing the isoelectric pH of a material to form a self-assembled layer having nanometer thickness.

Another object of embodiments of the present invention is to provide a method for increasing the thickness of the self-assembled layer.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the apparatus for determining the isoelectric pH of a material, hereof, includes: a first chamber adapted for containing a solution having a chosen pH including: a circular disk having an axis, a first face, and an opposing second face onto which the material is disposed; a shaft attached to the first face of the disk; a first reference electrode disposed in the vicinity of the second face of the disk and in the vicinity of the axis; and a hollow tube affixed to a wall of the first chamber at an orifice therein; a second chamber in fluid communication with the first chamber through the tube, including a second reference electrode; means for rotating the shaft at a chosen rate; and means for measuring the potential difference between the first reference electrode and the second reference electrode.

In another aspect of the present invention and in accordance with its objects and purposes, the method for determining the isoelectric pH of a material, hereof, includes: affixing the material onto one face of a circular disk having an axis of rotation and disposed in a solution having a selected pH value in a first chamber; rotating the disk at a chosen rate; measuring the potential difference between a first reference electrode disposed in the vicinity of both the axis of the disk and the material and a second reference electrode disposed in a second chamber in fluid communication through a tube with said first chamber; adjusting the pH of the solution such that the potential difference is approximately equal to the resting potential difference between the first reference electrode and the second reference electrode; and measuring the pH of the solution when the potential difference is approximately equal to the resting potential difference.

In yet another aspect of the present invention and in accordance with its objects and purposes, the method for depositing a coating material onto a substrate, hereof, includes: determining the isoelectric pH of the substrate; determining the isoelectric pH of the coating material; preparing a solution of the coating material having a pH between the isoelectric pH of the substrate and the isoelectric pH of the coating material; and immersing the substrate into the solution for a time sufficient for self-assembly of the coating material onto the substrate.

Benefits and advantages of embodiments of the present invention include, but are not limited to, providing a method for measuring the isoelectric pH of materials whereby the pH may be determined for which the electrostatic formation of a solid electrolyte coating on a substrate is advantageous since the growth of the coating is self-limiting because once the surface charge has been neutralized there is no longer a driving force for the solid electrolyte coating thickness to increase, and since uniform coatings without pinhole defects will be produced because a local driving force for assembly will exist if any bare electrode material is exposed to the solution. The present self-assembly procedure, when combined with electrodeposition, may be used to increase the coating thickness. Self-assembly, with or without additional electrodeposition, allows intimate contact between the anode, electrolyte and cathode which is required for successful application to solid-state batteries, as an example.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION OF THE INVENTION

Briefly, embodiments of the present invention include an apparatus and method for measuring the isoelectric pH for materials deposited on or otherwise affixed to and in contact with an electrode surface. Another embodiment of the invention is to provide a method for utilizing the isoelectric pH to form nanometer thickness, self-assembled layers on such materials. If the self-assembled thickness proves to be insufficient, an apparatus and method is provide for increasing the layer thickness by utilizing electrochemical methods in cooperation with self-assembly to obtain the desired properties.

Figure 1:
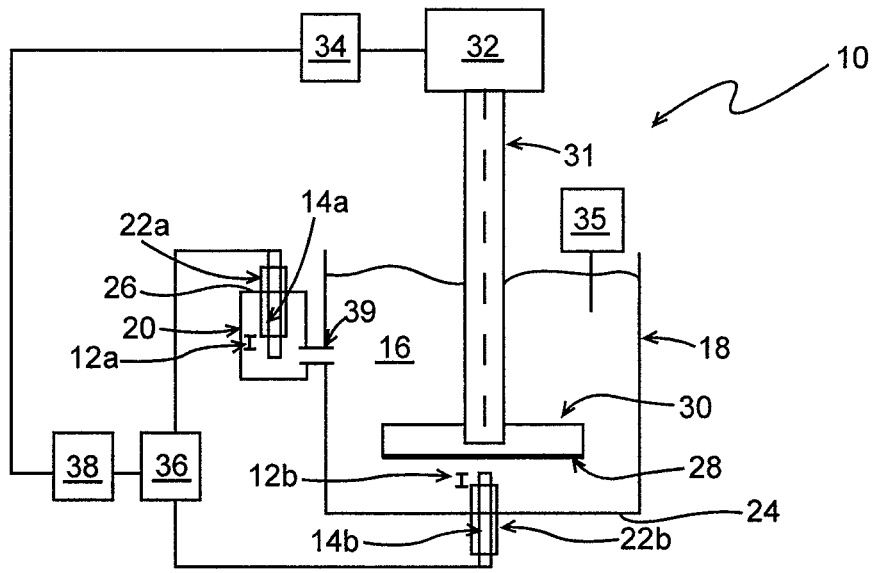
FIG. 1 is a schematic representation of an embodiment of the present apparatus for determining the isoelectric pH.

Reference will now be made in detail to the present embodiments of the invention, examples of which are illustrated in the accompanying drawings. In the FIGURES, similar structure will be identified using identical reference characters. Turning now to FIG. 1, a schematic representation of an embodiment of the present apparatus, 10, for determining the isoelectric pH is illustrated. Lengths of about 1 mm, 12a, 12b, of silver wire reference electrodes, 14a, 14b, are coated with AgCl and exposed to aqueous solution, 16, contained in cylindrical chamber, 18, having rectangular secondary chamber, 20, in fluid communication therewith. Clearly, other chamber geometries may be employed. Leak-proof, insulating material, 22a, 22b, covers silver wires 14a, 14b as these wires passes through walls, 24, and 26, of chamber 18 and secondary chamber 20. Material to be coated, 28, is affixed to circular disk, 30, mounted on shaft, 31, which is supported and turned by motor, 32, controlled by motor controller, 34. Means, 35, for measuring the pH of solution 16 are provided. Voltmeter or potentiometer, 36, measures the potential difference between AgCl-coated silver wires 14a and 14b, which is recorded on data processor, 38, which also controls motor controller 34.

Since the isoelectric pH is not a function of the material morphology or final geometric configuration, the use of a planar electrode surface in the apparatus is advantageous. Chamber 18 is filled with a solution containing a supporting electrolyte, for example, potassium chloride (KCl). Generally, the solvent will be water, as pH is most applicable to aqueous solutions. However, other solvents, or combinations of solvents, may be used, including aqueous solutions with other water-miscible solvents. Electrolyte solutions not containing water may also be employed where a supporting electrolyte has sufficient solubility to produce adequate conductivity for the electrolyte system; that is, the supporting electrolyte concentration must be sufficiently high that the solution resistance does not affect the potential readings of the two reference electrodes 14a and 14b. Electrolyte concentration must be sufficiently low such that when reference electrode 14b is placed in the vicinity of material to be coated 28, the aggregation of charged species in solution (often referred to as the diffuse or boundary layer), having opposite charge to that of the surface of material 28, can be detected. Any electrolyte species that, when dissolved, meets these criteria may be used. The concentration of the electrolyte is generally between 0.001 and 100 mM. It should be noted, however, that the electrolyte concentration chosen, even within this range, will affect the ability to detect the aggregation of charged species near the surface of the material of interest.

Reference electrode 14b is disposed in the center of chamber 18. While other reference electrodes may be used, an Ag wire having an electrodeposited AgCl film was used for the present EXAMPLE. Insulating jacket 22b surrounding Ag wire 14b assures that only a small portion 12b (approximately 1 mm) of reference electrode 14b is exposed to the liquid containing the supporting electrolyte 16. The area of the electroactive surface of material to be coated 28 exposed to solution 16 is chosen to be sufficiently large as to minimize edge effects. A minimum area is on the order of approximately 1 $cm^2$ for a circular disk. The maximum diameter of the electrode structure (disk plus material to be coated) was chosen to be smaller than the diameter of the inner wall surface of the main chamber by approximately 20%, assuming a cylindrical chamber, to eliminate unwanted effects from solution interaction with the chamber walls. While the gap between rotating disk 30 and the main chamber inner wall surface can be made larger, a substantially smaller gap may adversely affect the measurements. The material to be coated 28 may have a diameter of about 5 cm.

Once the disk has been prepared, it is attached to shaft 31 which may be rotated by motor 32 at speeds between zero and tens of thousands of rpm. Faster spin rates facilitate the measurements as a larger potential drop is induced between the reference electrodes as the spin rate is increased. The disk/shaft assembly is placed in chamber 18 assuring that the center of disk 30 is directly over reference electrode 14b at a distance≤1 mm, the reference electrode being placed as close as possible to spinning disk 30 such that the aggregation of charged species on material surface 28, which will be different than the equilibrium distribution in the bulk fluid, induces a potential difference between the two reference electrodes which can readily be detected. The reference electrode need not penetrate the diffuse layer, however.

Secondary chamber 20 in fluid communication with chamber 18 through tube, 39, permits solution 16 from chamber 18 to enter and leave, contains second reference electrode 14a. Openings in wall 26, not shown in FIG. 1, permit pressure equalization between chamber 18 and secondary chamber 20, thereby facilitating fluid movement between the two chambers. The secondary chamber isolates reference electrode 14a from the convective mass transfer of ions dissolved in solution 16 that is induced by the spinning disk assembly. Reference electrode 14a may have the same construction as the reference electrode 14b, ensuring that there is approximately zero potential difference between the electrodes before disk 30 is placed in solution. However, reference electrode 14a may be based on any redox chemistry for which the potential difference between that electrode and the reference electrode 14b is known (hereinafter referred to as the "resting potential difference"), and vice versa, as long as both reference electrodes act identically with respect to voltage changes in the spatial location of charged species in solution. In practice, less than about 0.1 mV resting potential difference is advantageous.

To determine the isoelectric pH of material 18, using apparatus 10 of FIG. 1 hereof, electrolyte solutions are prepared at different pH values. The disk assembly was spun at a chosen angular velocity in a solution with a selected pH and the potential difference between reference electrodes 14a and 14b was measured using a digital multimeter, as an example of an effective potential difference measurement apparatus. In general, higher spin rates provide better results, but rates>0 rpm to about 10,000 rpm are effective. Since the measured potential difference is dependent on the spin rate, measurements may be taken as a function of spin rate at a given pH to improve the accuracy of the data. Such measurements are repeated for solutions having different pH values until the measured potential difference between the reference electrodes is equal to zero or equal to the resting potential difference for reference electrodes having dissimilar redox potentials. This is the isoelectric pH of the material. A single solution where the pH is adjusted by small additions of acid, base, buffer, etc. between measurements, may also be used.

Figure 5:
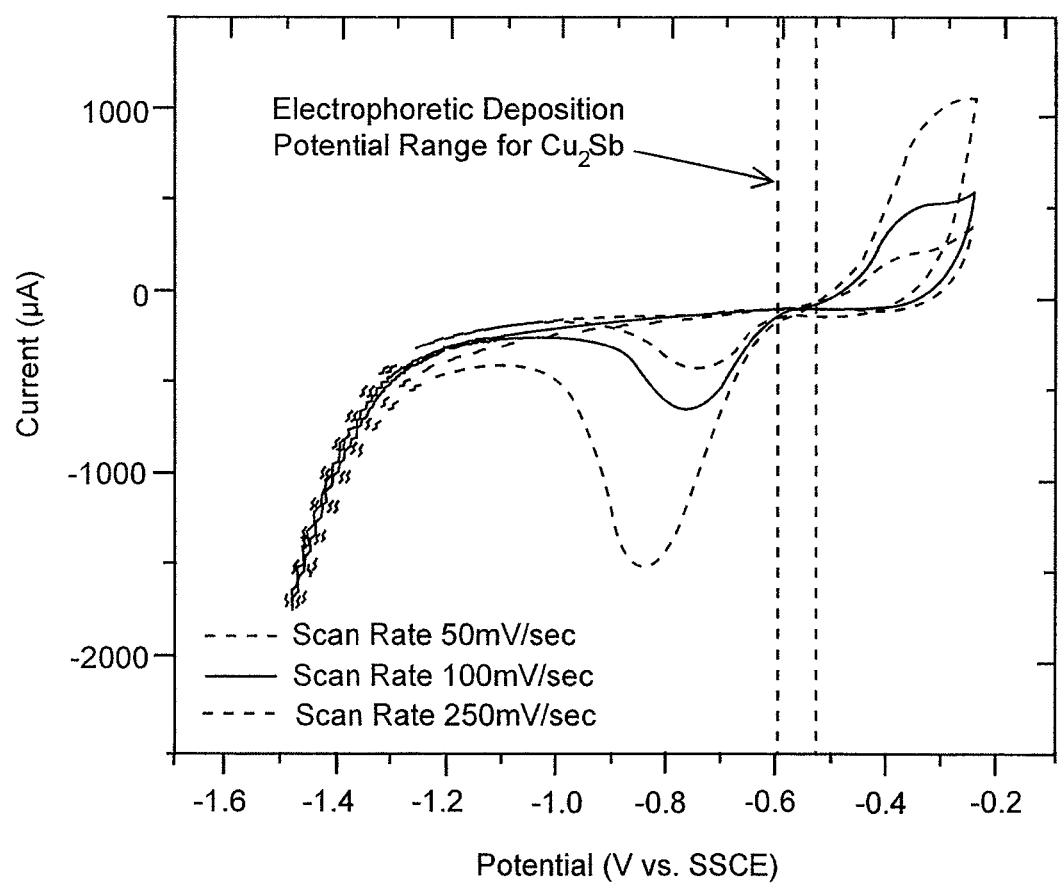
FIG. 5 is a graph of the current as a function of the applied potential, showing cyclic voltamograms for $Cu_2Sb$ in an $AlPO_4$ deposition solution.

Returning to apparatus 10 of FIG. 1, as stated hereinabove, reference electrode 14a disposed in secondary chamber 20 is separated from solution 16 in chamber 18 by tube 39 such that the ions in solution from both chambers can communicate without the influence of convective mass transfer. This has resulted in measured potential differences an order of magnitude higher than what is typically reported by Paul J. Sides and James D. Hoggard in "Measurement of the Zeta Potential of Planar Solid Surfaces by Means of a Rotating Disk," Langmuir 2004, 20, 11493-11498. As an example, Sides and Hoggard reports differences on the order of 0.1 my; whereas, differences on the order of a millivolt (FIG. 5 of Sides and Hoggard) are observed by Sides and Hoggard in only the most advantageous conditions, and for materials with high zeta potentials. Potential differences measured using apparatus 10 of FIG. 1 hereof are typically on the order of mV, as may be observed in FIG. 2, hereof, which is a graph of the measured potential difference as a function of the pH of the solution for $Cu_2Sb$ as material 28. The typical measured potential differences between the two reference electrodes reported by Side and Hoggard are difficult to distinguish from noise; thus, the embodiment described herein alleviates the most severe constraint of Sides and Hoggard, that the measurements are recorded at solution concentrations of less than about 1 mM. These solutions generate less than a 0.1 mV difference between the reference electrodes, which is difficult to quantitatively distinguish from noise for such measurements.

Another embodiment of the present invention is to use the measured isoelectric pH for the deposition of an electrolyte separation layer. Once the isoelectric pH for a material has been determined by the above-described procedure, or obtained from other sources thereof, solid-state ceramics which have shown to be electrically insulating but ionically conducting at nanoscale thicknesses may be self-assembled onto both anode and cathode materials. Example materials are $AlPO_4$, $Al_2O_3$, ZnO, and $Bi_2O_3$. $AlPO_4$ has been shown by other investigators to function as a solid-state electrolyte for lithium-ion batteries. Self-assembly methodology includes: (1) dissolving the appropriate precursors for the solid-state electrolyte in an aqueous solution; (2) adjusting the solution pH so that it is between the isoelectric pH of the electrode material, and that for the desired solid-state electrolyte, for which the isoelectric pH values are available in the literature; and (3) contacting the electrode material which can now be of any morphology and in any geometric configuration with the solution. The driving force for the self-assembly is electrostatics, where the overall net charge on the surface of the electrode material is opposite to the charge on the surface of the solid-state electrolyte. The above-mentioned ceramic and oxide materials can exist in solution as a colloidal suspension, and the surface charge of the material is controlled by the solution pH. Selection of the solution pH approximately midway between the isoelectric pH electrode material and that of the desired solid-state electrolyte material (coating material) generates coatings having the strongest binding to the substrate (the electrode material). For some applications, it may be useful to select a pH other than midway between the isoelectric pH of the two materials in order to vary the thickness of the film, despite the loss of some adhesion strength of the coating to the electrode. Generally however, the solution pH should be somewhere between the respective isoelectric pH values. Coatings typically form in approximately 30 min., although shorter times are possible if electrostatic equilibrium has been reached.

Electrostatic formation of a solid electrolyte coating is advantageous. First, the growth of the coating is self-limiting because once the surface charge has been neutralized there is no longer a driving force for the solid electrolyte coating thickness to increase. Anticipated thicknesses for the resulting coatings using this methodology are between about 1 and 20 nm (typically, on the order of 5 nm), and can be somewhat adjusted by choosing the pH and/or applied potential (as will be discussed hereinbelow). Second, uniform coatings without pinhole defects will be formed because a local driving force for assembly will exist if any bare electrode material is exposed to the solution. The results of self-assembled $AlPO_4$ deposited using the apparatus and method disclosed hereinabove demonstrate that uniform coatings having mechanical stability can be formed at ambient pressure and temperature from aqueous solutions. This apparatus and procedure can be used to coat a broad range of materials with varying morphologies and surface areas with coatings that can be tailored to provide the mechanical, electrical, and/or ionic conductivity properties of interest.

As will be set forth in detail in the EXAMPLES hereinbelow, if the thickness obtained from self-assembly is insufficient to stop electron tunneling or is otherwise insufficiently insulating, a slight overpotential (generally in the range between about one millivolt and about one volt, but typically between 10 and 100 mV) can be applied to increase the thickness of the coating through an electrodeposition procedure. Chronoamperometry or a pulsed chronoamperometry is expected to initiate an electrophoretic mechanism for the above-mentioned ceramics. Other electrodeposition techniques may also prove to be effective.

Having generally described embodiments of the present invention, the following example provides additional details.

EXAMPLE 1

Figure 2:
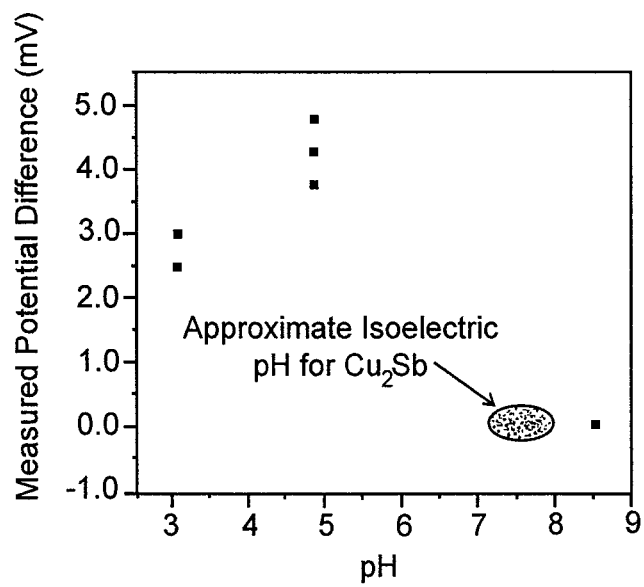
FIG. 2 is a graph of the measured potential difference as a function of pH for $Cu_2Sb$ in a 1 mM KCl solution using the apparatus of FIG. 1.

Using electrodeposition, $Cu_2Sb$ (an anode material for lithium-ion batteries) was deposited on a copper circular disk with a diameter of approximately 5 cm in accordance with J. M. Mosby and A. L. Prieto, Direct Deposition of $Cu_2Sb$ for Lithium-Ion Battery Anodes," J. Am. Chem. Soc. 2008, 130, 10656-10661. A stainless steel shaft was connected to the disk and installed in apparatus 10 of FIG. 1, hereof. The isoelectric pH of the $Cu_2Sb$ was determined using 1 mM KCl as the supporting electrolyte, Ag/AgCl as the reference electrodes, and a spin rate of approximately 750 rpm. The pH of the solution was controlled by adding either dilute hydrochloric acid to lower the pH or dilute ammonium hydroxide to increase the pH. Other reagents may be employed to adjust the solution pH. The isoelectric pH of $Cu_2Sb$ was determined to be approximately 7.5 (FIG. 2, hereof).

The reported isoelectric pH reported for $AlPO_4$ is 4.7 (See, e.g., J. Liu and A. Manthiram, Understanding the Improvement in the Electrochemical Properties of Surface Modified 5 V $LiMn_{1.42}Ni_{0.42}Co_{0.16}O_4$ Spinel Cathodes in Lithium-Ion Cells," Chem. Mater. 2009 21, 1695-1707). Therefore, the pH of the electrodeposition solution is about 6.1, the midpoint between the isoelectric pH of $AlPO_4$ and $Cu_2Sb$. This solution pH assures the maximum magnitude of opposite surface charges on the $AlPO_4$ and $Cu_2Sb$ to promote self-assembly since, as the solution pH becomes increasingly positive, that is, more basic, when compared to the isoelectric pH, the magnitude of the net surface charge becomes increasingly negative. Conversely, when the solution pH becomes increasingly negative, that is, more acidic, the magnitude of the net surface charge becomes increasingly positive.

$AlPO_4$ was coated onto $Cu_2Sb$ thin films that had been electroplated onto copper substrates by self-assembly in a solution described in EXAMPLE 2, hereof including approximately 2 mM of $NH_4H_2PO_4$ (ammonium phosphate monobasic), 1.8 mM of $Al(NO_3)_3 \cdot 9 H_2O$ (aluminum nitrate nonahydrate), and the pH was adjusted to 6.1 using $NH_4OH$ (ammonium hydroxide). The concentrations of the two precursors were in an approximately 1:1 molar ratio of $NH_4H_2PO_4$ to $Al(NO_3)_3 \cdot 9 H_2O$, and in millimolar concentrations, in order to avoid agglomeration of the colloids once the pH is adjusted.

Figure 3:
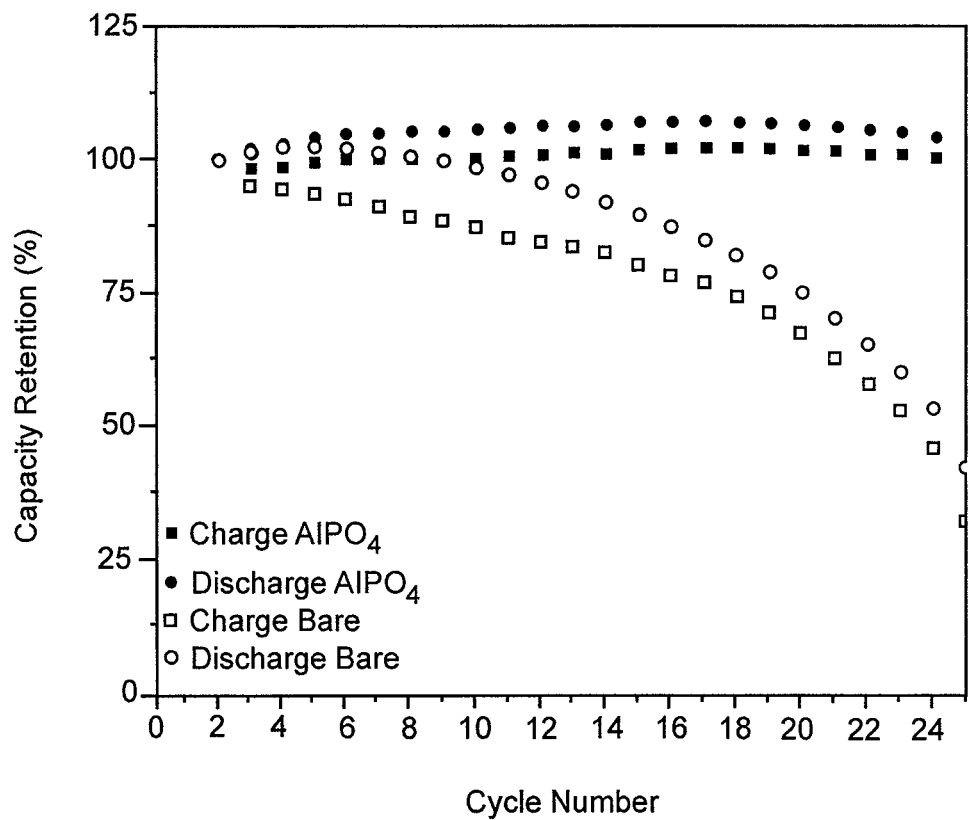
FIG. 3 is a graph of the capacity retention in percent as a function of the number of charging and discharging cycles for a $Cu_2Sb$ anode and $LiCoO_2$ cathode in 1M $LiClO_4$ in a solution of ethyl carbonate, dimethyl carbonate and diethyl carbonate in a 1:1:1 ratio, for coated and uncoated $Cu_2Sb$.

X-ray photoelectron spectroscopy (XPS) and scanning electron microscopy (SEM) coupled with energy dispersive spectroscopy (EDS) techniques were used to confirm that $AlPO_4$ self assembly onto the $Cu_2Sb$ had occurred. Although XPS peaks from Al and P confirm that $AlPO_4$ had self-assembled, Sb and Cu XPS peaks were observed to also be present, indicating a thin $AlPO_4$ layer. Negative electrodes having bare $Cu_2Sb$, and $Cu_2Sb$ coated with self-assembled $AlPO_4$ were tested in full cells with a $LiCoO_2$ cathode based positive electrode in a liquid electrolyte consisting of 1M $LiClO_4$ in ethylene carbonate (EC), dimethyl carbonate (DMC) and diethyl carbonate (DEC) in a (1:1:1) ratio by volume. The negative electrode modified with $AlPO_4$ showed much better capacity retention than the bare negative electrode during cycling as shown in FIG. 3, indicating that self-assembled $AlPO_4$ provides mechanical stability during cycling, thereby reducing the capacity loss that is found from material pulverization and material loss from volume expansion and other electrochemical processes associated with cycles of charging and discharging. The solid squares and circles of FIG. 3 show the charge and discharge capacity retention of the cell with the negative electrode comprising $Cu_2Sb$ covered with self-assembled $AlPO_4$, respectively, while the open boxes and circles show the charge and discharge capacity retention for cells having bare $Cu_2Sb$ anodes, respectively. Cells were charged and discharged between 2.75 and 3.35 V.

To ensure that the $AlPO_4$ coating was robust, SEM images and EDS spectra were collected after electrochemical cycling. SEM images of uncoated $Cu_2Sb$ films electrodeposited onto a copper substrate before electrochemical cycling showed the cubic morphology of the $Cu_2Sb$, while SEM images of a $Cu_2Sb$ electrodeposited film coated with $AlPO_4$ by self-assembly clearly showed the $AlPO_4$ coating. To establish the presence of the aluminum and phosphorous in the coated $Cu_2Sb$, and the absence of these elements in the uncoated $Cu_2Sb$, EDS spectra of the respective films were collected. EDS spectra of the uncoated $Cu_2Sb$ confirmed the presence only of copper and antimony with trace amounts of oxygen and carbon due to a thin oxide layer, and graphitic carbon on the $Cu_2Sb$ surface, respectively. The EDS spectra for the $AlPO_4$ coated $Cu_2Sb$ verified the presence of aluminum and phosphorous in addition to the elements identified for the uncoated film. The observed presence of chlorine is due to residual lithium perchlorate, $LiOCl_4$, from the electrochemical cycling experiments.

EXAMPLE 2

The combination of the self-assembly procedure described hereinabove with electrodeposition to increase the coating thickness, is now described with a $Cu_2Sb$ substrate coated with $AlPO_4$ as an example.

In order to increase the solid electrolyte coating thickness using an electrodeposition procedure, the bare electrode material is physically attached to a current collector, such as copper foil. The self-assembled coating is then added using the above-described procedure. Once self-assembly is complete, a counter and reference electrode may be placed in the solution and the electrode material attached to the current collector is made the working electrode. A potential is then applied to the working of the correct polarity with respect to the open circuit potential. The potential polarity will be specific to the electrode and solid electrolyte material, and is applied until the current decays to a desired value, most often approximately zero. The magnitude and polarity of the applied potential compared to the open circuit potential; the time for which the potential is applied; and the pH of the solution are three independent variables that will determine the rate at which the solid electrolyte coating will be deposited, and the final thickness of the coating. While one may conduct electrodeposition at the pH for which the self-assembly occurs, other pH values may be employed.

Figure 4:
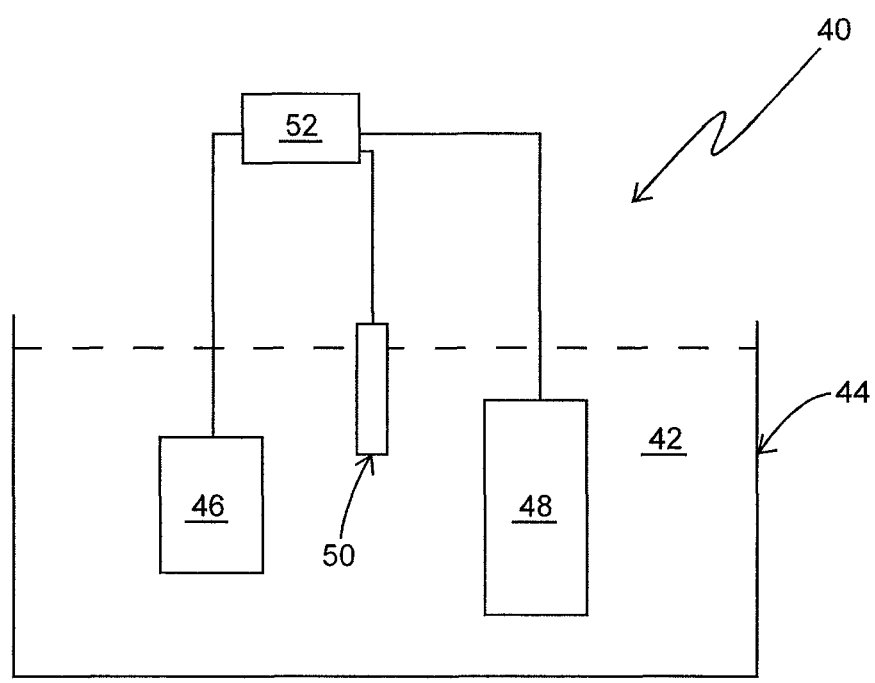
FIG. 4 is a schematic representation of an embodiment of an electrophoretic apparatus used to increase the deposited coating thickness.

FIG. 4 is a schematic representation of an embodiment of the electrophoretic deposition apparatus, 40, used to increase the $AlPO_4$ coating thickness. Electrophoretic deposition implies that charged particles (such as for a suspension of colloidal particles having a net surface charge) are moving in response to an applied external electric field, while electrodeposition implies that current is being passed to initiate a chemical reaction from an electrode resulting in a deposition of material onto the electrode. An $AlPO_4$ deposition solution, 42, is placed in deposition chamber, 44, containing working electrode, 46 ($Cu_2Sb$ that has been electrodeposited onto a copper substrate, in this example), counter electrode, 48 (platinum in this case, but other materials such as stainless steel may also be used), and reference electrode, 50 (sodium saturated calomel electrode (SSCE), as an example). Potentiostat/galvanostat, 52, applies voltage between working electrode 46 and counter electrode 48, and measures the current flowing therebetween. Potentiostat/galvanostat, 52 also measures the voltage between working electrode 46 and reference electrode 50.

The placement of the electrodes and their spatial relationship to each other may affect the deposition process. To determine the potential range, with respect to the open circuit potential (OCP), cyclic voltamograms of $Cu_2Sb$ in $AlPO_4$ deposition solution were plotted in FIG. 5. The $Cu_2Sb$ was electroplated onto a copper current collector having a surface area of 0.32 cm$^2$. The OCP is defined as the potential at which no current passes through the cell. For this system, a potential window of approximately 75 mV exists as illustrated by the vertical dashed lines. The electrodeposition solution was the same as that for the self-assembly solution, but supporting electrolytes may be added facilitate transfer of charged species. However, supporting electrolytes are chosen such that they do not undergo redox reactions or other detrimental processes under the electrodeposition conditions used to increase the coating thickness, thereby adversely affecting the deposition.

$AlPO_4$ was coated onto $Cu_2Sb$ thin films that had been electroplated onto copper substrates by self-assembly in the solution set forth in EXAMPLE 1, hereof. Once the self-assembly process is completed, electrodeposition may be used to increase the $AlPO_4$ coating thickness. In this example, electrophoretic deposition is appropriate, although other electrodeposition techniques may be utilized. Two conditions were chosen: (a) 30 mV more positive than the OCP; (b) 30 mV more negative than the OCP. These potentials were chosen because they both are within the range determined from the cyclic voltamograms contained in FIG. 5. Additionally, the more positive potential is expected to induce a positive surface charge on the $Cu_2Sb$ whereas the negative potential a negative surface charge. To compare the effect of applying a positive and negative potential when compared to the OCP, X-Ray Photoelectron Spectroscopy (XPS) was used since it is a quantitative surface sensitive characterization technique.

Figure 6:
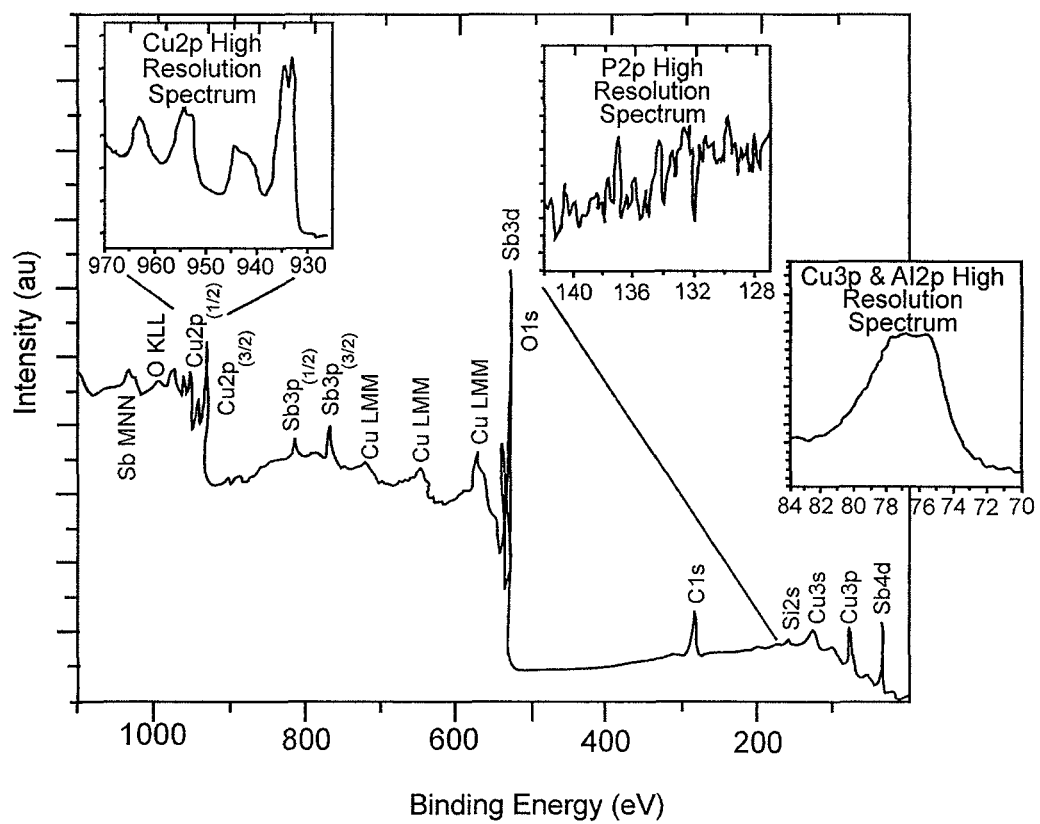
FIG. 6 shows a survey X-Ray Photoelectron Spectrum (XPS) for electroplated $Cu_2Sb$, and high-resolution spectra for the copper 2p, phosphorous 2p, and aluminum 2p regions.
Figure 7:
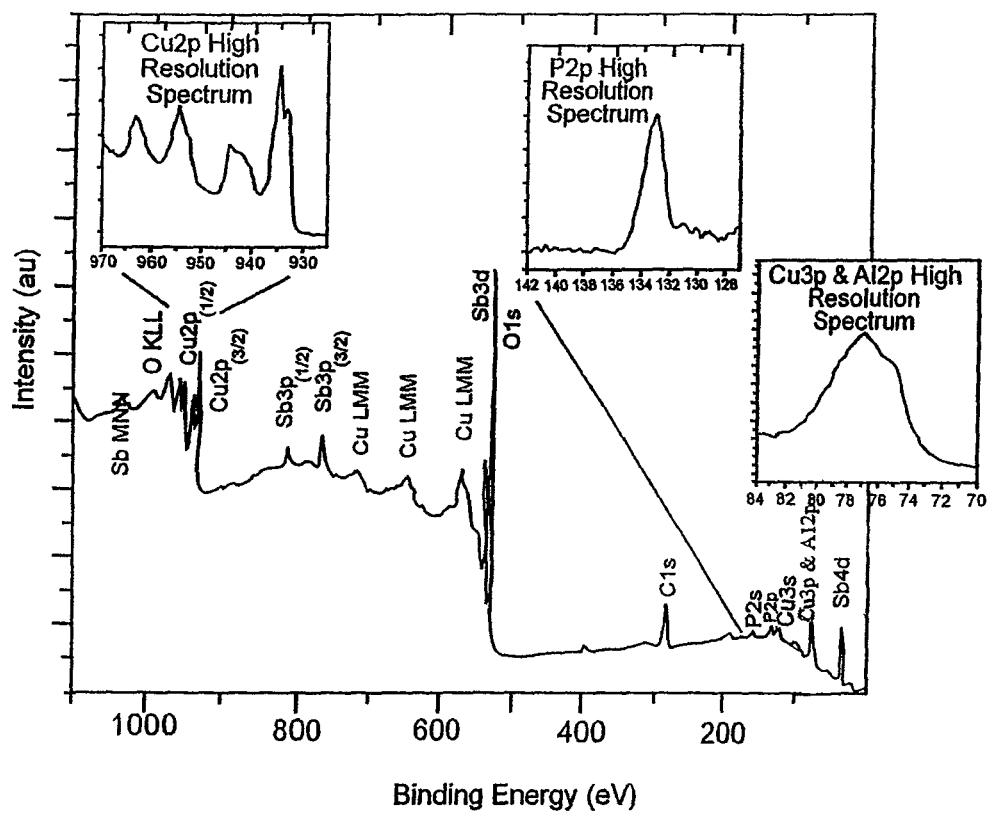
FIG. 7 shows a survey XPS spectrum of a coating formed with a positive applied potential after the self-assembly process had been completed, and high-resolution spectra for the copper 2p, phosphorous 2p, and aluminum 2p regions for electroplated $Cu_2Sb$ having a self-assembled $AlPO_4$ coating.

FIG. 6 shows XPS spectra of electroplated $Cu_2Sb$. The survey spectrum and high resolution spectra do not show the presence of aluminum or phosphorous, which confirms that an $AlPO_4$ coating is not present. Note that the region of the phosphorous 2p and aluminum 2p peaks are in close proximity to copper 3s and copper 3p peaks, respectively. FIG. 7 shows XPS spectra of a coating formed with a positive applied potential after the self-assembly process had been completed. A clear difference between the spectra in FIGS. 6 and 7 may be observed. In the phosphorous 2p region of FIG. 7, a peak is present, while for FIG. 6 a peak in the same region is not observed. Additionally, this peak may be located in the survey spectrum in close proximately to the copper 3s peak; the phosphorous 2p peak is equivalent in magnitude to the copper 3s peak. When analyzing the aluminum 2p region in FIG. 7, the peak shape has changed due to the presence of the aluminum 2p peak when compared to the same region plotted in FIG. 6.

Figure 8:
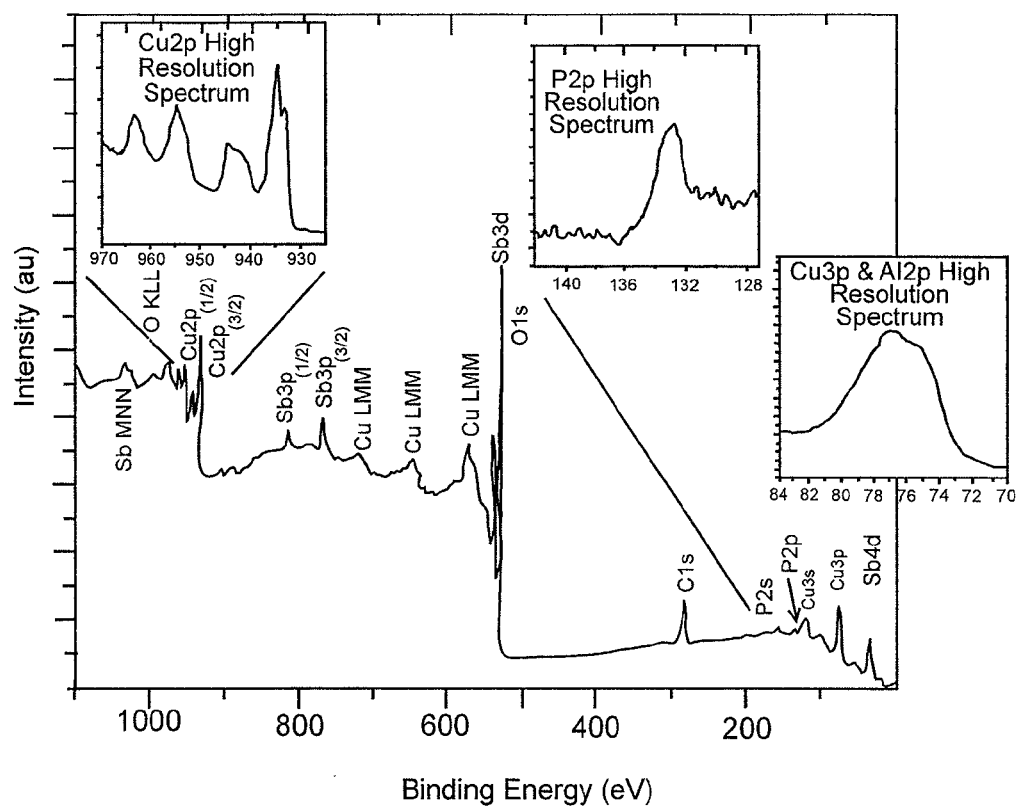
FIG. 8 shows a survey XPS spectrum of a coating formed with a negative applied potential after the self-assembly process had been completed, and high-resolution spectra for the copper 2p, phosphorous 2p, and aluminum 2p regions for electroplated $Cu_2Sb$ having a self-assembled $AlPO_4$ coating.

FIG. 8 shows XPS spectra of a coating formed with a negative applied potential after the self-assembly process had been completed. By observing the phosphorous 2p region, these XPS spectra are more indicative of an $AlPO_4$ coating that has been self-assembled onto the surface of $Cu_2Sb$ without the addition of an applied potential. While a peak is observed in both the high-resolution and survey spectra, the peak is approximately half the magnitude of the copper 3s peak. Applying a negative potential when compared to the OCP, therefore, does not increase the coating thickness when compared to a coating that has been self-assembled using the procedures described hereinabove. This is likely the result of the application of a negative potential inducing a negative surface charge. Since the net surface charge of the $AlPO_4$ in solution is also negative, there is insufficient driving force to promote the assembly of additional $AlPO_4$ onto the $Cu_2Sb$ surface to increase the coating thickness. By contrast, applying a positive potential when compared to the OCP results in a positive surface charge which produces in an increase in the $AlPO_4$ coating thickness. This is confirmed by the phosphorous 2p peak in FIG. 7 which is approximately twice the magnitude of the peak contained in FIG. 8 when using the copper 3s peak as a reference. Since XPS is a quantitative surface sensitive technique, the increase in the phosphorous 2p peak magnitude when compared to the copper 3s peak is indicative of an increase in the surface $AlPO_4$ coating thickness.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for depositing an $AlPO_4$ coating material having a first isoelectric pH onto a $Cu_2Sb$ substrate having a second isoelectric pH, comprising the steps of:
    preparing a solution of precursors of the coating material;
    adjusting the pH of the solution to between the second isoelectric pH and the first isoelectric pH after said step of preparing the solution of precursors of the coating material;
    immersing the substrate in the solution;
    whereby a coating having a thickness is generated by self-assembly of the coating material onto the substrate and
    increasing the thickness of the coating on the substrate by electrophoretic deposition of additional coating material onto the self-assembled coating by applying a positive voltage relative to open circuit potential.

2. The method of claim 1, wherein the pH of the solution is approximately the average of the second isoelectric pH and the first isoelectric pH.

3. The method of claim 1, wherein the solution of the coating material for said electrophoretic deposition is the same solution used for said self-assembly of said coating material.

* * * * *